United States Patent
Bencherif

(10) Patent No.: US 10,507,190 B2
(45) Date of Patent: *Dec. 17, 2019

(54) METHOD FOR TREATING HYPERHIDROSIS WITH DEXMECAMYLAMINE

(71) Applicant: Atacama Therapeutics, Inc., Wellesley, MA (US)

(72) Inventor: Merouane Bencherif, Winston-Salem, NC (US)

(73) Assignee: Atacama Therapeutics, Inc., Wellesley, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/019,690

(22) Filed: Jun. 27, 2018

(65) Prior Publication Data

US 2018/0369168 A1    Dec. 27, 2018

Related U.S. Application Data

(63) Continuation of application No. 15/505,414, filed as application No. PCT/US2015/046055 on Aug. 20, 2015, now Pat. No. 10,080,726.

(60) Provisional application No. 62/040,477, filed on Aug. 22, 2014.

(51) Int. Cl.
*A61K 31/13* (2006.01)
*A61K 9/00* (2006.01)
*A61K 9/20* (2006.01)

(52) U.S. Cl.
CPC ........... *A61K 31/13* (2013.01); *A61K 9/0053* (2013.01); *A61K 9/20* (2013.01)

(58) Field of Classification Search
CPC ........ A61K 31/13; A61K 9/0053; A61K 9/20
See application file for complete search history.

(56) References Cited

U.S. PATENT DOCUMENTS

| | | |
|---|---|---|
| 5,986,142 A | 11/1999 | Magni et al. |
| 7,101,916 B2 | 9/2006 | Shytle et al. |
| 8,901,177 B2 | 12/2014 | Bencherif et al. |
| 10,080,726 B2 | 9/2018 | Bencherif |
| 2004/0044083 A1 | 3/2004 | Shytle et al. |
| 2013/0253067 A1* | 9/2013 | Bencherif .............. A61K 31/13 514/661 |

FOREIGN PATENT DOCUMENTS

| | | |
|---|---|---|
| JP | 2002-532392 A | 10/2002 |
| WO | WO-00/35279 A1 | 6/2000 |
| WO | WO-2013/142162 A1 | 9/2013 |

OTHER PUBLICATIONS

De-Moura et al. (Ann Thorac Surg 2013, 95, pp. 465-471).*
Beckel et al., "Expression of functional nicotinic acetylcholine receptors in rat urinary bladder epithelial cells," Ann J Physiol Renal Physiol. 290 (1): 20 pages (2006).

(Continued)

*Primary Examiner* — Savitha M Rao
(74) *Attorney, Agent, or Firm* — Clark & Elbing LLP

(57) ABSTRACT

The present invention relates to dexmecamylamine and the use of dexmecamylamine, substantially free of exo-R-mecamylamine, in the treatment of hyperhidrosis.

18 Claims, 10 Drawing Sheets

Primary hyperhidrosis is associated with increased sympathetic cholinergic activity

(56) References Cited

OTHER PUBLICATIONS

Bibevski et al., "Functional Nicotinic Acetylcholine Receptors That Mediate Ganglionic Transmission in Cardiac Parasympathetic Neurons," J Neurosci. 20(13): 5076-5082 (2000).

Briggs et al., "Effect of MK-801 at the Human alpha 7 Nicotinic Acetylcholine Receptor," Neuropharmacology. 35(4): 407-414 (1996).

Chiari et al., "Sex Differences in Cholinergic Analgesia I: A Supplemental Nicotinic Mechanism in Normal Females," Anesthesiology. 91(5):1447-54 (1999).

De Moura et al., "Preservation of Alpha-3 Neuronal Nicotinic Acetylcholine Receptor Expression in Sympathetic Ganglia After Brain Death," Mol Neurobiol. 45(2): 362-365 (2012).

De Moura Júnior et al., "Expression of acetylcholine and its receptor in human sympathetic ganglia in primary hyperhidrosis," Ann Thorac Surg. 95(2):465-70 (2013).

De Oliveira et al., "Morphometric Analysis of Thoracic Ganglion Neurons in Subjects with and without Primary Palmar Hyperhidrosis," Ann Vasc Surg. 28(4): 1023-9 (2014).

Extended European Search Report for European Application No. 15833912.7, dated Mar. 5, 2018 (6 pages).

Horch et al., "Perisynaptic Surface Distribution of Multiple Classes of Nicotinic Acetylcholine Receptors on Neurons in the Chicken Ciliary Ganglion," J Neurosci. 15(12): 7778-7795 (1995).

Jacob et al., "The Ultrastructural Localization of alpha-Bungarotoxin Binding Sites in Relation to Synapses on Chick Ciliary Ganglion Neurons," J Neurosci. 3(2): 260-271 (1983).

Kurzen et al., "Phenotypical and Molecular Profiling of the Extraneuronal Cholinergic System of the Skin," J Invest Dermatol. 123(5): 937-949 (2004).

Lukas, "Diversity and Patterns of Regulation of Nicotinic Receptor Subtypes," Ann N Y Acad Sci. 757: 153-168 (1995).

Papke et al., "Analysis of Mecamylamine Stereoisomers on Human Nicotinic Receptor Subtypes," J Pharmacol Exp Ther. 297(2): 646-656 (2001).

Skok, "Nicotinic acetylcholine receptors in autonomic ganglia," Auton Neurosci. 97(1): 1-11 (2002).

Stone et al., "Chemistry and structure-activity relationships of macamylamine and derivatives," J Med Pharm Chem. 5(4): 665-690 (1962).

Utsugisawa et al., "Changes with aging and ischemia in nicotinic acetylcholine receptor subunit alpha7 mRNA expression in postmortem human frontal cortex and putamen," Neurosci Lett. 270(3): 145-148 (1999).

Xu et al., "Population Pharmacokinetics of TC-5214, a Nicotinic Channel Modulator, in Phase I and II Clinical Studies," J Clin Pharmacol. 54(6): 707-718 (2014).

Iwase et al., "Altered response in cutaneous sympathetic outflow to mental and thermal stimuli in primary palmoplantar hyperhidrosis," J Auton Nerv Syst. 64(2-3): 65-73 (1997).

\* cited by examiner

TC-5214 potency increases with increased firing frequency

Summary of hyperhidrosis etiologies

Sites of actions of TC-5214
Sympathetic innervation (pre- and post-ganglionic)

Sites of actions of TC-5214
Sweat gland

Contrast between primary and secondary hyperhidrosis (sympathetic and vasomotor contribution)

Overactive parasympathetic and sympathetic in OAB

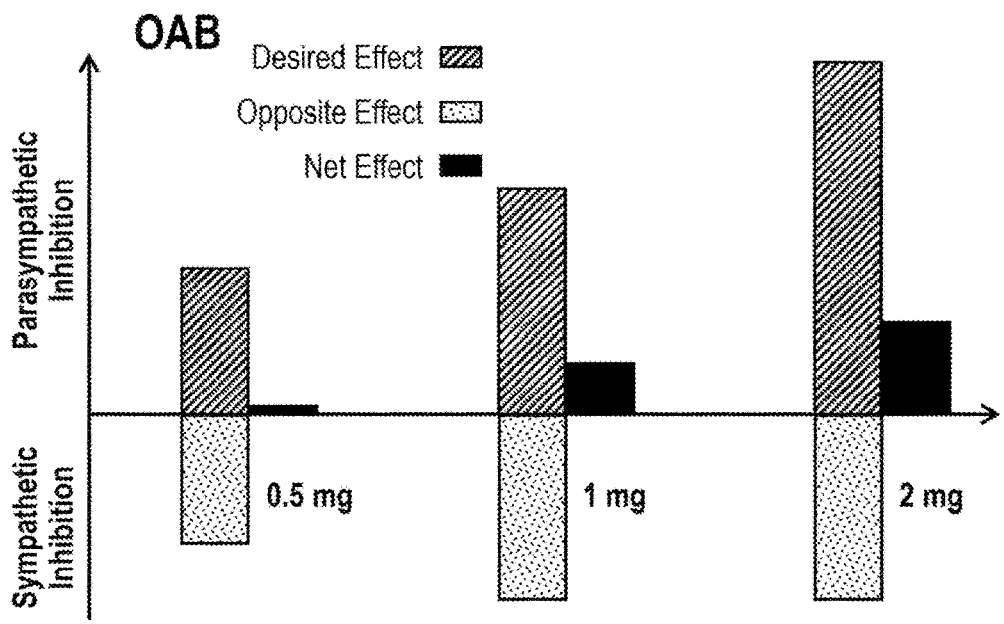

Summary of all the know effects which shows the major differences between the 2 conditions. For OAB all the effects are mediated through control of 2 antagonistic overactive pathways: the sympathetic which is more sensitive to TC-5214 but less powerful than the parasympathetic. The lower doses have counteracting effects and the progressive inhibition of the overactive parasympathetic tilts the balance toward relaxation but comes at a cost (constipation, urinary infection). For PH we are dealing with one overactive pathway (the sympathetic) which is very sensitive to TC-5214.

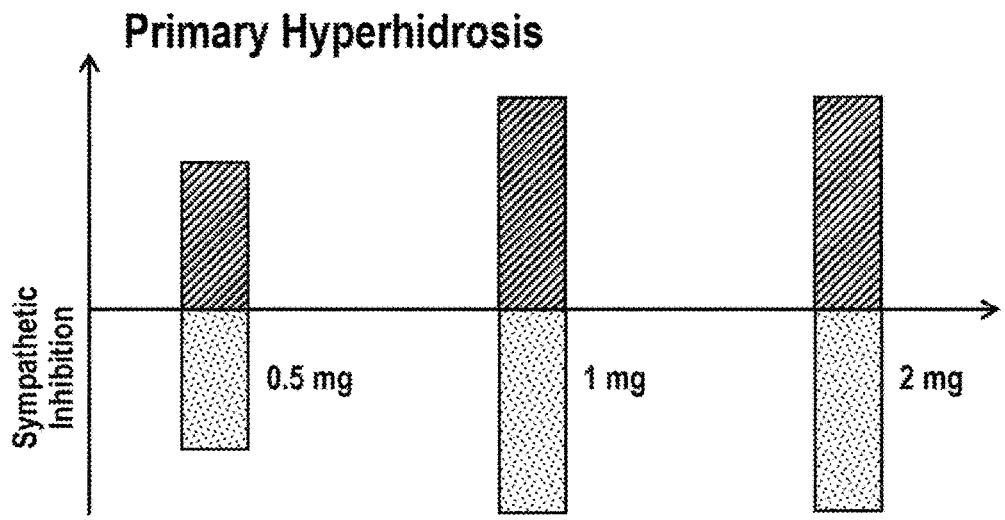

*Fig. 7*

Anticipated theoretical outcome in OAB and hyperhidrosis based on known contribution of sympathetic and parasympathetic innervation to the bladder and sympathetic only to the sweat glands (sympathetic has a weak contribution to relaxation and is slightly more sensitive to TC-5214 than the parasympathetic which has a strong contribution to contraction of the bladder).

| Hyperhidrosis Disease Severity Scale ||
|---|---|
| "How would you rate the severity of your hyperhidrosis?" ||
| ☐ 1. | My sweating is never noticeable and never interferes with my daily activities |
| ☐ 2. | My sweating is tolerable but sometimes interferes with my daily activities |
| ☐ 3. | My sweating is barely tolerable and frequently interferes with my daily activities |
| ☐ 4. | My sweating is intolerable and always interferes with my daily activities |

Tips and Usage Information for Clinicians

The Hyperhidrosis Disease Severity Scale (HDSS) is a disease-specific, quick, and easily-understood diagnostic tool that provides a qualitative measure of the severity of the patient's condition based on how it affects daily activities. The questions that make up the scale my be posed to the patient in written or interview form.

Ask the patient to select the statement above that best reflects his or her experience with sweating of the specified body area. Next to each statement is a number. These numbers indicate how responses should be scored. A score of 3 or 4 indicates severe hyperhidrosis. A score of 1 or 2 indicates mild or moderate hyperhidrosis. Post-treatment, as part of a measurement of treatment efficacy and patient satisfaction, the HDSS may be administered again. A 1-point improvement in HDSS score has been associated with a 50% reduction in sweat production and a 2-point improvement with an 80% reduction.

The validity and reliability of the HDSS have been analyzed using three studies and been found to have strong to moderate correlations with the Hyperhidrosis Impact Questionnaire (HHIQ), Dermatology Quality of Life Index (DLQI), and gravimetric sweat production measurements.

*Fig. 8*

Reference: A Comprehensive Approach to the Recognition, Diagnosis, and Severity-Based Treatment of Focal Hyperhidrosis: Recommendations of the Canadian Hyperhidrosis Advisory Committee, Dermatologic Surgery, August 2007, pages 908-923

|  | Al Salts | Botox | Muscarinic antagonists | Microwave Thermolysis | Surgery (T3, T4 ...) | TC-5214 |
|---|---|---|---|---|---|---|
|  |  | Approved | Off-label |  |  |  |
| Axillary | Yes | Yes | Yes | Yes | Yes | Yes |
| Palmoplantar | No | No | Yes | No | Yes | Yes |
| Face scalp | No | No | Yes | No | No | Yes |
| Generalized | No | No | Yes | No | No | Yes |
| Side effects | ++ (severe dermatitis, tolerance) | + | +++ Dry mouth, blurred vision, constipation, drowsiness, and tachycardia. | + | ++ | Little to none at <2mg |
| Compensatory | Yes | Yes | ? | Yes | Yes | No |

51% had palmoplantar and axillary hyperhidrosis
30% had palmar and plantar hyperhidrosis,
9% have axillary alone
6% had palmoplantar and facial hyperhidrosis
5% had all areas involved Only 9% of patients have axillary alone

*Fig. 9*

METHOD FOR TREATING HYPERHIDROSIS WITH DEXMECAMYLAMINE

CROSS REFERENCE TO RELATED APPLICATION

This application claims priority to U.S. provisional application No. 62/040,477 filed Aug. 22, 2014, the contents of which are hereby incorporated by reference.

FIELD OF THE INVENTION

The present invention relates to exo-S-mecamylamine and the use of exo-S-mecamylamine in medical treatments.

BACKGROUND OF THE INVENTION

Hyperhidrosis is a condition characterized by abnormally increased sweating or perspiration, in excess of that required for regulation of body temperature. Hyperhidrosis is associated with a significant quality of life burden from a psychological, emotional, and social perspective. As such, it has been referred to as a "silent handicap." Hyperhidrosis is a medical condition in which a person sweats excessively and unpredictably. People with hyperhidrosis may sweat even when the temperature is cool or when they are at rest. Estimates provide that at least 3% of the global population suffers from hyperhidrosis (also known as excessive sweating, excessive perspiration, or diaphoresis), namely at least about 211 million people.

Hyperhidrosis can either be generalized or localized to specific pails of the body. Hands, feet, armpits, and the groin area are among the most active regions of perspiration due to the relatively high concentration of sweat glands. When excessive sweating is localized (e.g., palms, soles, face, underarms, scalp) it is referred to as primary or focal hyperhidrosis. Generalized or secondary hyperhidrosis usually involves the body as a whole and is the result of an underlying condition.

Hyperhidrosis can also be classified depending by onset, either congenital or acquired. Focal hyperhidrosis is found to start during adolescence or even before and seems to be inherited as an autosomal dominant genetic trait. Primary or focal hyperhidrosis must be distinguished from secondary hyperhidrosis, which can start at any point in life. The latter form may be due to a disorder of the thyroid or pituitary glands, diabetes mellitus, tumors, gout, menopause, certain drugs, or mercury poisoning.

Hyperhidrosis may also be divided into palmoplantar (symptomatic sweating of primarily the hands or feet), gustatory, generalized and focal hyperhidrosis.

Alternatively, hyperhidrosis may be classified according to the amount of skin affected and its possible causes. In this approach, excessive sweating in an area greater an 100 cm$^2$ (16 sq in) (up to generalized sweating of the entire body) is differentiated from sweating that affects only a small area.

Primary focal hyperhidrosis refers to excessive sweating that is not caused by another medical condition, nor is it a side effect of medications. The excessive sweating is the medical condition. This type of sweating occurs on very specific areas of the body (described as focal areas) and may be relatively "symmetric," in that both the left and light sides of the body are affected similarly. As noted above, the most common focal areas are the hands, feet, underarms, and head or face. Primary focal hyperhidrosis often begins in childhood or adolescence, especially hyperhidrosis of the hands and feet. Interestingly, although people with primary focal hyperhidrosis have episodes of excessive sweating at least once a week, they usually do not experience excessive sweating white sleeping. Primary focal hyperhidrosis may be inherited and many members of the same family may suffer from this condition.

Symptoms associated with primary focal hyperhidrosis include one or more, and in particular two or more of: (i) sweat is bilateral and relatively symmetrical, meaning a subject sweats the same amount on both sides of the body; (ii) excess sweat impairs daily activities; (iii) at least one episode a weak, (iv) onset of excess sweat is earlier than age 25; (v) a positive family history, namely other members of the subject's family suffer from similar sweating problems; and (vi) the is no excess sweating when asleep. Some dermatologists believe upwards of 90 percent of people who present with excessive sweating will be diagnosed with primary hyperhidrosis.

The other main type of hyperhidrosis is referred to as secondary generalized hyperhidrosis. This type of excessive sweating is caused by another medical condition or is a side affect of a medication. Unlike with primary focal hyperhidrosis, people with secondary hyperhidrosis experience sweating on larger or other areas of the body, described as generalized areas. Another key difference between the two types of hyperhidrosis is that people with secondary generalized hyperhidrosis may often experience their sweating symptoms while sleeping. With secondary hyperhidrosis, excessive sweating usually starts in adulthood, whereas primary hyperhidrosis starts in childhood or adolescence. Finding a potential treatment for secondary excessive sweating often involves first determining what, if any, underlying medical condition or medication may be the root of the problem. Conditions that cause second hyperhidrosis include: Acromegaly, Anxiety conditions, Cancer, Carcinoid syndrome, Certain medications and substances of abuse, Glucose control disorders, Heart disease, Hyperthyroidism: Lung disease; Menopause; Parkinson disease; Pheochromocytoma; Spinal cord injury; Stroke; and Tuberculosis or other infections.

The primary symptom of hyperhidrosis is wetness. Visible signs of sweating may be noted during a doctor's visit. Tests may also be used to diagnose excessive sweating, including: (i) Starch-iodine test: an iodine solution is applied to the sweaty area; after it dries, starch is sprinkled on the area; the starch-iodine combination turns a dark blue color wherever there is excess sweat; and (ii) Paper test: special paper is placed on the affected area to absorb the sweat, and then weighed; the heavier, the more sweat has accumulated.

Current treatments may include:

Antiperspirants: Excessive-sweating may be controlled with strong anti-perspirants, which plug the sweat ducts. Products containing 10% to 20% aluminum chloride hexahydrate are the first line of treatment for underarm sweating. Some patients may be prescribed a product containing a higher dose of aluminum chloride, which is applied nightly onto the affected areas. Antiperspirants can cause skin irritation, and large doses of aluminum chloride can damage clothing.

Iontophoresis: This procedure uses electricity to temporarily turn off the sweat gland. It is most effective for sweating of the hands and feet. The hands or feet are placed into water, and then a gentle current of electricity is passed through it. The electrically is gradually increased until the patient feels a light tingling sensation. The therapy lasts about 10 to 20 minutes and requires several sessions. Side effects include skin cracking and blisters, although rare.

Botox: Botulinum toxin type A (Botox) is used to treat severe underarm sweating. Botulinum toxin is injected into the underarm to temporarily block the nerves that stimulate sweating. Side effects include injection-site pain and flu-like symptoms. Botox used for sweating of the palms can cause mild, out temporary weakness and intense pain.

Endoscopic thoracic sympathectomy (ETS): In severe cases, a minimally-invasive surgical procedure called sympathectomy may be recommended when other treatments do not work. The procedure turns off the signal that tells the body to sweat excessively. It is usually done on patients whose palms sweat much more heavily than normal it may also be used to treat extreme sweating of the face. ETS does not work as well for those with excessive armpit sweating.

Surgery: This is surgery to remove the sweat glands in the armpits. Methods used include laser, curettage (scraping), excision (cutting), or liposuction. These procedures are done using local anesthesia.

Alternative options, including oral medications, are needed with different safety, metabolic, tolerability, and efficacy profiles to effectively treat hyperhidrosis.

Mecamylamine (N2,3,3-tetramethylbicyclo[2.2.1] heptan-2-amine hydrochloride), was developed and characterized by Merck & Co., Inc., as a ganglionic blocker with clinically significant hypotensive actions (Stone et al., *Chemistry and structure-activity relationships of mecamylamine and derivatives*, J. Med. Pharm. Chem., 5(4):665-690. 1962). Mecamylamine was sold under the tradename Inversine®. Depending on preferred naming convention, the chemical name for mecamylamine may also be N,2,3,3-tetramethylnorbornan-2-amine. Mecamylamine exists as a racemic mixture of enantiomers and can be obtained according to the methods and processes described in U.S. Pat. No. 5,986,142, incorporated herein by reference for its teaching regarding methods of producing mecamylamine.

Unique characteristics of mecamylamine, including oral efficacy for treating hypertension, rapid onset, long duration of action, and nearly complete absorption from the gastrointestinal tract, made the drug a more desirable alternative to the then-existing ganglionic blockers. The average total daily dose of Inversine® (mecamylamine hydrochloride) used to treat high blood pressure was 25 mg, usually administered in three divided doses. The safety/tolerability profile of mecamylamine in humans has been established during decades of clinical use as an antihypertensive agent. The most common adverse reactions to the marketed drug include constipation, orthostatic dizziness, urinary retention, and blurred vision.

U.S. Pat. No. 7,101,916, herein incorporated by reference, provides for a pharmaceutical composition that includes a therapeutically effective amount of exo-S-mecamylamine or a pharmaceutical acceptable salt thereof, substantially free of exo-R-mecamylamine, in combination with a pharmaceutically acceptable carrier, wherein the pharmaceutical composition is characterized by a higher overall therapeutic index than a substantially similar pharmaceutical composition comprising, exo-R-mecamylamine substantially free of exo-S-mecamylamine. The medical conditions disclosed therein include but are not limited to substance addiction (involving nicotine, cocaine, alcohol, amphetamine, opiate, other psychostimulant and a combination thereof), aiding smoking cessation, treating weight gain associated with smoking cessation, hypertension, hypertensive crisis, herpes type I and II, Tourette's Syndrome and other tremors, cancer (such as small cell lung cancer), atherogenic profile, neuropsychiatric disorders (such as bipolar disorder, depression, anxiety disorder, panic disorder, schizophrenia, seizure disorders, Parkinson's disease and attention deficit hyperactivity disorder), chronic fatigue syndrome, Crohn's disease, autonomic dysreflexia, and spasmogenic intestinal disorders. Hyperhidrosis is not described or disclosed in U.S. Pat. No. 7,101,916. The patent discloses that exo-S-mecamylamine may be administered intravenously, intramuscularly, transdermally, intrathecally, orally or by bolus injection. The dosage of exo-S-mecamylamine for treating the identified diseases is described in a range of about 0.5 mg to about 1000 mg, depending on dosage form, and exo-mecamylamine may be administered one to four times per day. Examples include a dose of about 2.5 mg per day for adults with drug-resistant Tourette's Syndrome and 1 mg per day or less for a small child with mild ADHD.

Purified exo-S-mecamylamine and exo-R-mecamylamine can be obtained according to methods discussed in U.S. Pat. No. 7,101,916, and references cited therein, also incorporated herein by reference for their teaching regarding the production of purified mecamylamine enantiomers. Exo-S-mecamylamine may also be referred to as dexmecamylamine, S-mecamylamine, TC-5214, or (S)—N,2,3,3-tetramethylnorboran-2-amine, and includes a pharmaceutically acceptable salt thereof.

Dexmecamylamine is a use-dependent potent inhibitor of the $\alpha 3$ nicotinic receptor subtype (e.g., $\alpha 3\beta 2$ and $\alpha 3\beta 4$). Such receptors are expressed in the urothelium and regulate bladder smooth muscle contraction. (Beckel et al., *Expression of functional nicotinic acetylcholine receptors in rat urinary bladder epithelial cells*, Am. J. Physiol. Renal Physiol. 290; F103-110, 2006). A clinical study was performed to evaluate the safety, tolerability, and efficacy of dexmecamylamine (TC-5214) for the treatment of Overactive Bladder (OAB). The study included a three- or five-week screening period, followed by a 12-week treatment period during which patients received either one of three doses of dexmecamylamine or placebo twice daily, randomized in a ratio of 2:1:1:1 (placebo, low dose, mid dose, high dose), with a two-week follow-up period. A total of 768 subjects with overactive bladder were randomized into the double-blind treatment period of the study. On Jul. 28, 2014, Targacept announced top-line results from the Phase 2b clinical trial of TC-5214 as a treatment for overactive bladder (OAB). In the trial, the high dose of TC-5214 demonstrated mixed results on the co-primary endpoints by providing a statistically significant reduction in micturition frequency (p=0.033) and an improvement that did not reach statistical significance on episodes of urinary incontinence (p=0.379) per 24 hours, after 12 weeks of treatment. As a consequence of these results, Targacept discontinued further development of TC-5214 in OAB. In this trial, TC-5214 was considered generally safe and well tolerated. There was a placebo-corrected 15.1% rate of constipation and a 5.9% rate of urinary tract infection in the high dose group. See also, PCT Application No. PCT/US2013/030640, which published as WO 2013/142162 A1.

Dexmecamylamine, however, has not been studied previously in a model or study related to hyperhidrosis.

There remains a need for effective treatment of hyperhidrosis, with specific focus toward symptomatic relief, having an improved side effect and tolerability profile.

SUMMARY OF THE INVENTION

One aspect of the present invention includes a method of treating hyperhidrosis, the method comprising the administrate of a therapeutically effective amount of dexmecamylamine or a pharmaceutically acceptable salt thereof, substantially free of exo-R-mecamylamine, to a subject with hyperhidrosis.

One aspect of the present invention includes a method of treating hyperhidrosis, wherein the administration of dexmecamylamine is sufficient to reduce perspiration relative to baseline in the subject with hyperhidrosis.

One aspect of the present invention includes a method of treating hyperhidrosis, wherein the administration of dexmecamylamine is sufficient to affect sweating in a patient in at least one location with an HDSS change of ≥1. Preferably, the administration of dexmecamylamine is sufficient to affect sweating in a patient in at least two locations with an HDSS change of ≥0.5 in each. The locations may be selected from axillary, palmoplantar, face/scalp, and generalized.

One aspect of the present invention includes a method of treating hyperhidrosis, wherein the administration of dexmecamylamine provides efficacy without significant side effects in a subject with hyperhidrosis.

One aspect of the present invention includes a method of treating hyperhidrosis, the method comprising the oral administration of dexmecamylamine or a pharmaceutically acceptable salt thereof. In an amount from about 0.1 mg to about 2.0 mg, once a day, substantially free of exo-R-mecamylamine, to a subject with hyperhidrosis.

One aspect of the present invention includes a method of treating hyperhidrosis, wherein the dexmecamylamine or a pharmaceutically acceptable salt thereof is orally administered in an amount of about 0.1 mg, once daily.

One aspect of the present invention includes a method of treating hyperhidrosis, wherein the dexmecamylamine or a pharmaceutically acceptable salt thereof is orally administered in an amount of about 0.2 mg, once daily.

One aspect of this present invention includes a method of treating hyperhidrosis, wherein the dexmecamylamine or a pharmaceutically acceptable salt thereof is orally administered in an amount of about 0.5 mg, once daily.

One aspect of the present invention includes a method of treating hyperhidrosis, wherein the dexmecamylamine or a pharmaceutically acceptable salt thereof is orally administered in an amount of about 1.0 mg, once daily.

One aspect of the present invention includes a method of treating hyperhidrosis, wherein the dexmecamylamine or a pharmaceutically acceptable salt thereof is orally administered in an amount of about 2.0 mg, once daily.

One aspect of the present invention includes a method of treating hyperhidrosis, wherein the dexmecamylamine or a pharmaceutically acceptable salt thereof is orally administered in tablet form.

One aspect of the present invention includes a method of treating overactive bladder in a human.

The scope of the present invention includes methods, uses, compound for use, and compound for treating hyperhidrosis, as well as uses of compound for the manufacture of a medicament for treating hyperhidrosis.

The scope of the present invention is intended to encompass such inventions regardless of claim format.

The scope of the present invention includes all combinations of aspects, embodiments, and preferences herein described.

BRIEF DESCRIPTION OF THE FIGURES

FIG. 4A illustrates sympathetic innervation (pre- and post-ganglionic). FIG. 4B illustrates sweat gland site of action.

FIG. 7 illustrates a theoretical outcome in overactive bladder and hyperhidrosis based on the contribution of sympathetic and parasympathetic innervation to the bladder and sympathetic, only, innervation to the sweat glands; again, thereby illustrating that the results observed in the overactive bladder study support a hypothesis for use in hyperhidrosis.

FIG. 8 is a Hyperhidrosis Disease Severity Scale (HDSS) from the International Hyperhidrosis Society, with reference to the publication: A Comprehensive Approach to the Recognition, Diagnosis, and Severity-Based Treatment of Focal Hyperhidrosis: Recommendations of the Canadian Hyperhidrosis Advisory Committee, Dermatologic Surgery, August 2007, pages 908-923, herein incorporated by reference with regard to the diagnosis and symptoms of hyperhidrosis.

FIG. 9 is a summary table illustrating the benefits of a systemic approach with oral dexmecamylamine over standard approaches in hyperhidrosis patient care.

DETAILED DESCRIPTION OF THE INVENTION

Figure 1:
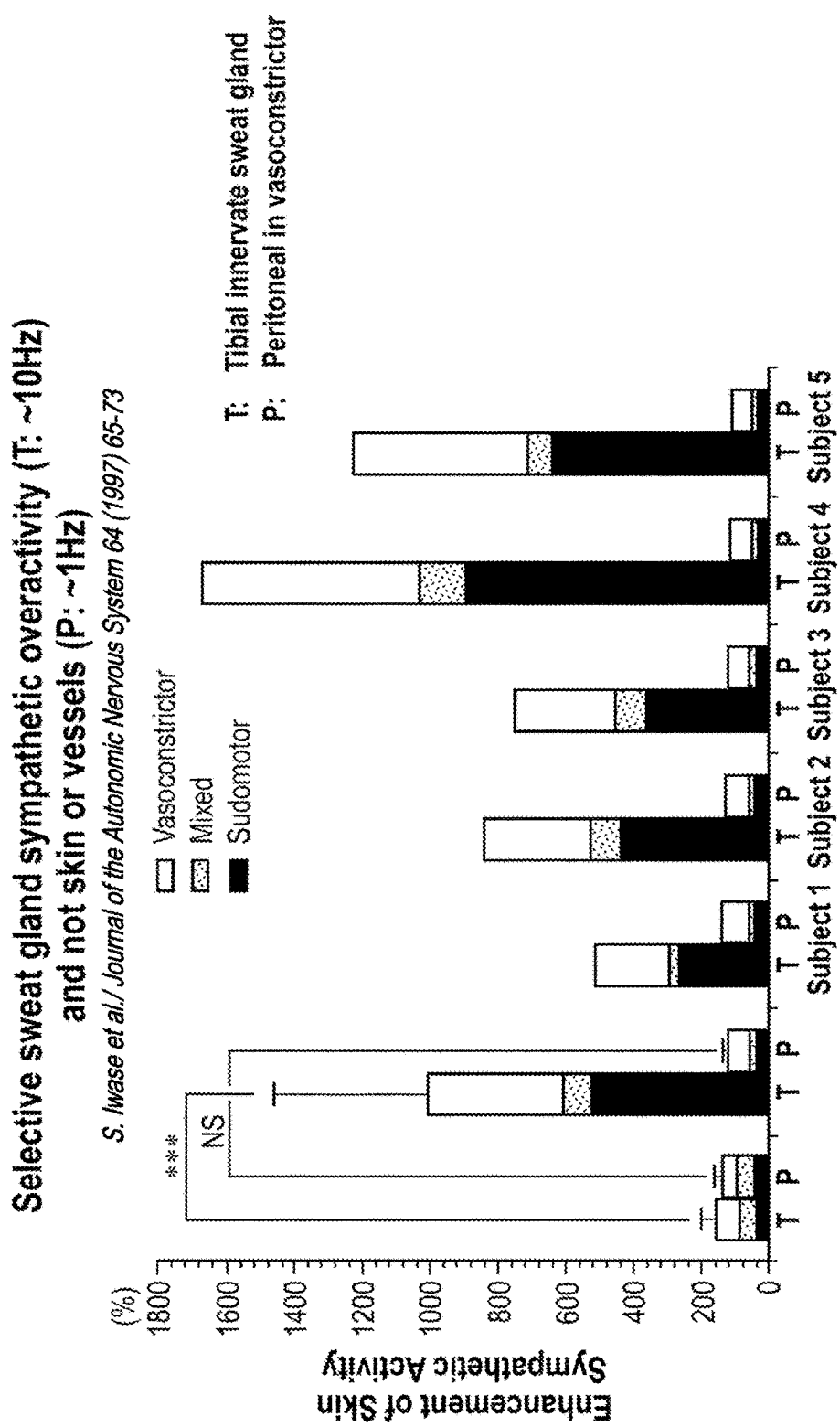
FIG. 1 illustrates that primary hyperhidrosis is associated with increased sympathetic cholinergic activity.

Dexmecamylamine is a selective nicotinic acetylcholine receptor (nAChR) channel modulator. While the precise molecular targets associated with effects on the bladder are still under investigation, dexmecamylamine functionally interacts with human $\alpha 4\beta 2$, $\alpha 3\beta 2$, and $\alpha 3\beta 4$ nicotinic receptors and the known interactions of dexmecamylamine with $\alpha 3$-containing nicotinic receptors suggests it is likely to prove beneficial in the treatment of OAB. Nonclinical studies with dexmecamylamine have been conducted to evaluate the potential for treatment in OAB, and clinical studies using dexmecamylamine for treating OAB are being proposed.

It has now been found that because dexmecamylamine is excreted almost entirely unchanged in the urine, dexmecamylamine reaches higher concentrations in the urine compared to the plasma. The exposure differential results in the ability of dexmecamylamine to target local nicotinic receptors in the urothelium that affect bladder contraction frequency while limiting systemic side effects. Consequently, the potential for dexmecamylamine to treat OAB through its action on nAChRs in the bladder urothelium warrants further investigation.

More recently, dexmecamylamine was evaluated as adjunctive therapy in the treatment of major depressive disorder (MDD) in a large international Phase 3 depression program. Although dexmecamylamine failed to demonstrate efficacy in the treatment of depression, the compound proved to be well tolerated at doses up to and including the top dose evaluated, 4 mg twice daily (BID). More than 2400 subjects have received dexmecamylamine in double-blind or open-label studies.

No safety studies using dexmecamylamine have been performed in OAB. Phase 2 and Phase 3 clinical studies using dexmecamylamine in Major Depressive Disorder (MDD) have been conducted and completed. Dexmecamylamine was generally safe and well-tolerated in these studies. Briefly, in the fixed dose Phase 3 studies in MDD, at doses of 2 mg BID (the maximum doses to be studied in the OAB study), the most frequent treatment emergent adverse events that were reported more than 2% more commonly in the dexmecamylamine group compared to placebo group were: constipation (15.2% dexmecamylamine vs. 3.8% placebo): and dry mouth (7.0% dexmecamylamine vs. 1.3% placebo). There were no noteworthy differences in any measurements of vital signs, blood or urine laboratory measurements, EGG conduction intervals, or suicidality. In these fixed dose studies, the treatment emergent adverse events reported for doses less then 2 mg BID are similar to placebo.

Additional pre-clinical studies on mecamylamine and its stereoisomers have demonstrated that dexmecamylamine provides a superior safety profile over mecamylamine and its R-isomer (see U.S. Pat. No. 7,101,916), but there have not been any previously published pre-clinical or clinical studies using dexmecamylamine to treat OAB or to assess the safety and efficacy profile for the OAB indication. Pre-clinical in vivo studies in rat models described herein support the safety and efficacy of using dexmecamylamine, substantially free of exo-R-mecamylamine, to treat OAB in humans with a favorable side effect profile. In short, it is unexpected that administration of relatively low systemic doses of dexmecamylamine, substantially free of exo-R-mecamylamine, in human patients will result in the safe and efficacious treatment of OAB.

Unless stated otherwise, the following terms and phrases as used herein are intended to have the following meanings. The fact that a particular term or phrase is not specifically defined should not be correlated to indefiniteness or lacking clarity, but rather terms herein are used within their ordinary meaning. When trade names are used herein, applicants intend to independently include the tradename product and the active pharmaceutical ingredient(s) of the tradename product.

For reference herein, "dexmecamylamine substantially free of exo-R-mecamylamine" includes dexmecamylamine in amounts greater than or equal to 95% by weight and exo-R-mecamylamine 5% or less by weight. More preferably, "dexmecamylamine substantially free of exo-R-mecamylamine" includes dexmecamylamine greater than or equal to 98% by weight and exo-R-mecamylamine 2% or less by weigh. More preferably, "dexmecamylamine substantially free of exo-R-mecamylamine" includes dexmecamylamine greater than or equal to 99% by weight and exo-R-mecamylamine 1% or less by weight. Even more preferably, "dexmecamylamine substantially free of exo-R-mecamylamine" includes exo-S-mecamylamine greater than or equal to 99.5% by weight and exe-R-mecamylamine 0.5% or less by weight. Most preferably, "dexmecamylamine substantially free of exo-R-mecamylamine" includes exo-s-mecamylamine greater than or equal to 99.7% by weight and exo-R-mecamylamine 0.3% or less by weight.

As used herein, the term "pharmaceutically acceptable" refers to carrier(s), diluent(s), excipient(s) or salt forms of the compound of the present invention that are compatible with the other ingredients of the formulation and not deleterious to the recipient of the pharmaceutical composition.

As used herein, the term "pharmaceutical composition" refers to the compound of the present invention optionally in combination with one or more pharmaceutically acceptable carriers, diluents, or excipients. Pharmaceutical compositions preferably exhibit a degree of stability to environmental conditions so as to make them suitable for manufacturing and commercialization purposes.

As used herein, the terms "effective amount", "therapeutically effective amount", and "effective dose" refer to an amount of the compound of the present invention sufficient to elicit the desired pharmacological or therapeutic effects, thus resulting in an effective treatment of hyperhidrosis.

Treatment of hyperhidrosis may be manifested by delaying or preventing the onset or progression of the disorder, as well as the onset or progression of symptoms associated with the disorder. Treatment of hyperhidrosis may also be manifested by a decrease or elimination of symptoms, reversal of the progression of the disorder, as well as any other contribution to the well-being of the patient.

In certain embodiments, the administration of dexmecamylamine, substantially free of exo-R-mecamylamine, can eliminate, ameliorate, reduce, relieve, or treat one or more symptoms of hyperhidrosis.

Two instruments are used as primary or secondary endpoints: the HDSS (Hyperhidrosis Disease Severity Scale, FIG. 8; score from 4 to 1) and the gravimetric method (paper to absorb sweat and weighted). Often, they are used in conjunction and linked. Ultimately, the subjective opinion of the patient is the focus, as noted in review of the HDSS scoring of FIG. 8. The extent of sweat inhibition is important, but also an important factor is the number of locations affected.

As illustrated in FIG. 9, the current standard of care for patients with hyperhidrosis affects sweating in only one location (e.g., axillary), have major side effects (e.g., off-label use of an anti-muscarinic with dry mouth), and most, if not all, treatments that reduce sweating in one location induce a compensatory increase in other regions. This is true even for surgery such as sympathectomy, which totally dries out one region and has a number of other issues.

The use of dexmecamylamine once-daily in an oral dose of 0.1 to 2 mg is believed to show a significant change in the HDSS at ≥2 locations, thus supporting the treatment of general primary hyperhidrosis. Regarding a measure of efficacy, efficacy at one, specific location with an HDSS change of ≥1 is needed. If more than one location is effected, then a change of 0.5 would be clinically meaningful.

The use of TC-5214 is believed to provide systemic availability of TC-5214 (as opposed to, e.g., Botox® treatment which needs to be infected thereby targeting only axillary regions).

The effective dose for hyperhidrosis can vary, depending upon factors such as the condition of the patient, the severity of the symptoms of the disorder, and the manner in which the pharmaceutical composition is administered. To be administered in an effective dose, compounds may be administered in an amount of as low as about 0.1 mg to about 4 mg; in certain embodiments, about 0.1 mg to 2 mg; in certain embodiments, about 0.2 mg to about 2 mg. Thus, an effective dose typically represents the amount that may be administered as a single dose, or as one or more doses that may be administered over a 24 hours period. In certain embodiments of the present invention an effective dose is about 0.25 mg, 0.5 mg, about 1 mg, or about 2 mg, as free base equivalents, once daily, orally.

In certain embodiments, one or more of the dosage strengths may include an optional 5.4 mg of Opadry® 03B 150008 Red per tablet for a non-functional film coat.

The present invention includes a salt or solvate of the compounds herein described, including combinations thereof such as a solvate of a salt. The compounds may exist in solvated, for example hydrated, as well as unsolvated forms, and the present invention encompasses all such forms. Typically, but not absolutely, the salts of the present invention are pharmaceutically acceptable salts. Salts encompassed within the term "pharmaceutically acceptable salts" refer to non-toxic salts of the compounds of this invention. Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, trimethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates. In certain embodiments, S-mecamylamine hydrochloride is a preferential salt form.

Although it is possible to administer the compound of the present invention in the form of a bulk active chemical, it is preferred to administer the compound in the form of a pharmaceutical composition or formulation. Thus, one aspect the present invention includes pharmaceutical compositions comprising dexmecamylamine and/or pharmaceutically acceptable salts thereof and one or more pharmaceutically acceptable carriers, diluents, or excipients. Another aspect of the invention provides a process for the preparation of a pharmaceutical composition including admixing dexmecamylamine and/or pharmaceutically acceptable salts thereof with one or more pharmaceutically acceptable carriers, diluents or excipients.

The manner in which the compound of the present invention is administered can vary. The compound of the present invention is preferably administered orally. Preferred pharmaceutical compositions for oral administration include tablets, capsules, caplets, syrups, solutions, and suspensions.

One embodiment of an oral pharmaceutical composition includes about 0.6 mg S-mecamylamine hydrochloride; about 6.1 mg microcrystalline cellulose, grade I; about 102.5 mg microcrystalline cellulose, grade II; about 6.0 mg hydroxypropyl cellulose; about 3.6 mg croscarmellose sodium; about 0.6 mg colloidal silicon dioxide; and about 0.6 mg magnesium.

One embodiment of a pharmaceutical composition includes about 1.2 mg S-mecamylamine hydrochloride; about 12.2 mg microcrystalline cellulose, grade I; about 95.8 mg microcrystalline cellulose, grade II; about 6.0 mg hydroxypropyl cellulose; about 3.6 mg croscarmellose sodium; about 0.6 mg colloidal silicon dioxide; and about 0.6 mg magnesium.

One embodiment of a pharmaceutical composition includes about 2.4 mg S-mecamylamine hydrochloride; about 24.4 mg microcrystalline cellulose, grade I; about 82.4 mg microcrystalline cellulose, grade II; about 6.0 mg hydroxypropyl cellulose; about 3.6 mg croscarmellose sodium; about 0.6 mg colloidal silicon dioxide; and about 0.6 mg magnesium.

One embodiment for manufacture includes blending and sieving the excipients as is known in the art.

The pharmaceutical compositions can also be administered via injection, namely, intravenously, intramuscularly, subcutaneously, intraperitoneal, intraarterially, intrathecally, and intracerebroventricularly. Intravenous administration is a preferred method of injection. Suitable carriers for injection are well known to those of skill in the art and include 5% dextrose solutions, saline, and phosphate buffered saline.

The formulations may also be administered using other means, for example, rectal administration. Formulations useful for rectal administration, such as suppositories, are well known to those of skill in the art. The compounds can also be administered by inhalation, for example, in the form of an aerosol; topically, such as, in lotion form; transdermally, such as, using a transdermal patch (for example, by using technology that is commercially available from Novartis and Alza Corporation), by powder injection, or by buccal, sublingual, or intranasal absorption.

Pharmaceutical compositions may be formulated in unit dose form, or in multiple or subunit doses. The pharmaceutical compositions may be administered to a patient or subject such as a warm-blooded animal for example, a mammal such as a mouse, rat, cat, rabbit, dog, pig, cow, or monkey; but advantageously is administered to a human being. In addition, the time of day (e.g., morning, evening, before bedtime) and the number of times per day (e.g., once per day, twice per day) that the pharmaceutical composition is administered can vary.

EXAMPLES

Example 1: TC-5214 (0.1 to 2 mg ONCE a Day) For the Improvement of Symptoms Associated with Primary Hyperhidrosis Hyperhidrosis is a medical condition with overactive sweat glands and primary hyperhidrosis (the target indication) refers to excessive sweating not caused by another medical condition or medications (secondary hyperhidrosis). TC-5214 may inhibit the overactive sympathetic cholinergic fibers innervating the sweat glands associated with primary hyperhidrosis. Efficacy may be found from between about 0.1 to about 2 mg oral administration of TC-5124, once daily.

TC-5214 has potential for symptomatic treatment of primary hyperhidrosis for several reasons, including (1) primary hyperhidrosis is associated with increased sympathetic cholinergic activity (the only input to sweat glands); (2) the potency of TC-5214 increases with increased firing frequency; (3) primary hyperhidrosis has minor vasomotor changes, if any; (4) sympathetic activity decreases at night in primary hyperhidrosis (but not secondary hyperhidrosis when it is aggravated) and TC-5214 use-dependent inhibition will also decrease at night; (5) reducing muscarinic responses on the sweat gland should lead to decreased acetylcholine output (i.e., sympathetic inhibition); and (6) inhibition of the nicotinic receptors present on the sweat glands, namely local inhibition. A once-a-day, low dose administration (0.1 to 2 mg) will be tested for the treatment of primary hyperhidrosis.

As illustrated in FIG. 1, one hypothesis provides that overactive sympathetic cholinergic fibers innervating sweat glands and target receptors on sweat glands may be inhibited at low doses (between about 0.1 and 2 mg per day). This is believed due, in part, to the fact that TC-5214 potency will increase with frequency due to its slow off-rate kinetics. See FIG. 2, which illustrates a 10-fold shift to the left with increasing frequency. The effective dose range, therefore, is believed to be between 0.1 and 1 mg; with a top dose at 2 mg once per day, since sympathetic activity decreases at night in primary hyperhidrosis.

Figure 2:
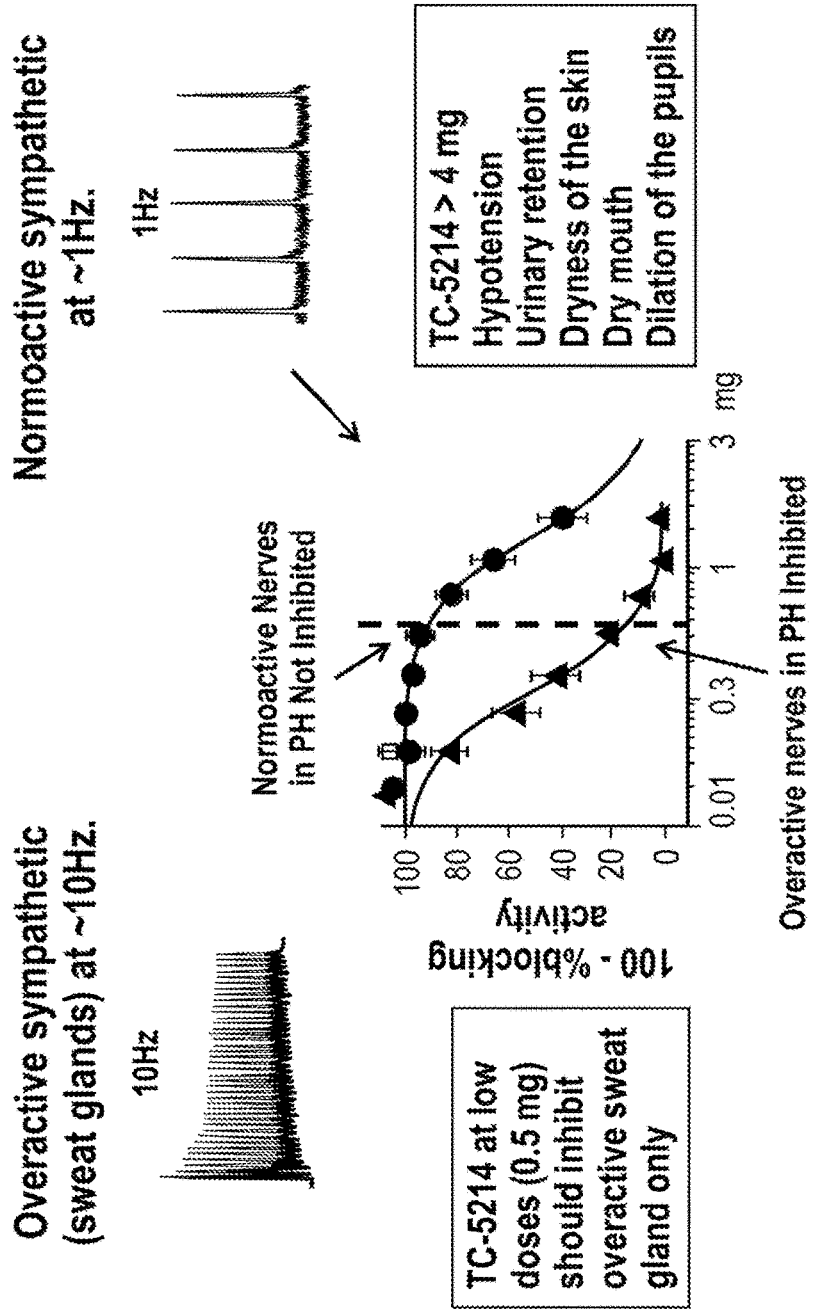
FIG. 2 illustrates a measure of TC-5214 potency increases with increased firing frequency.

As shown in FIG. 2, dose-responses for inhibition of sympathetic activities at low frequency (1 Hz in black/circle) and high frequencies (10 Hz in red/triangle). The potency of TC-5214 shifts to the left (red/triangle curve) thereby reducing sweating due to overactive sympathetic but remain too low to induce inhibition of the parasympathetic and associated side effects, including urinary retention and constipation.

Figure 3:
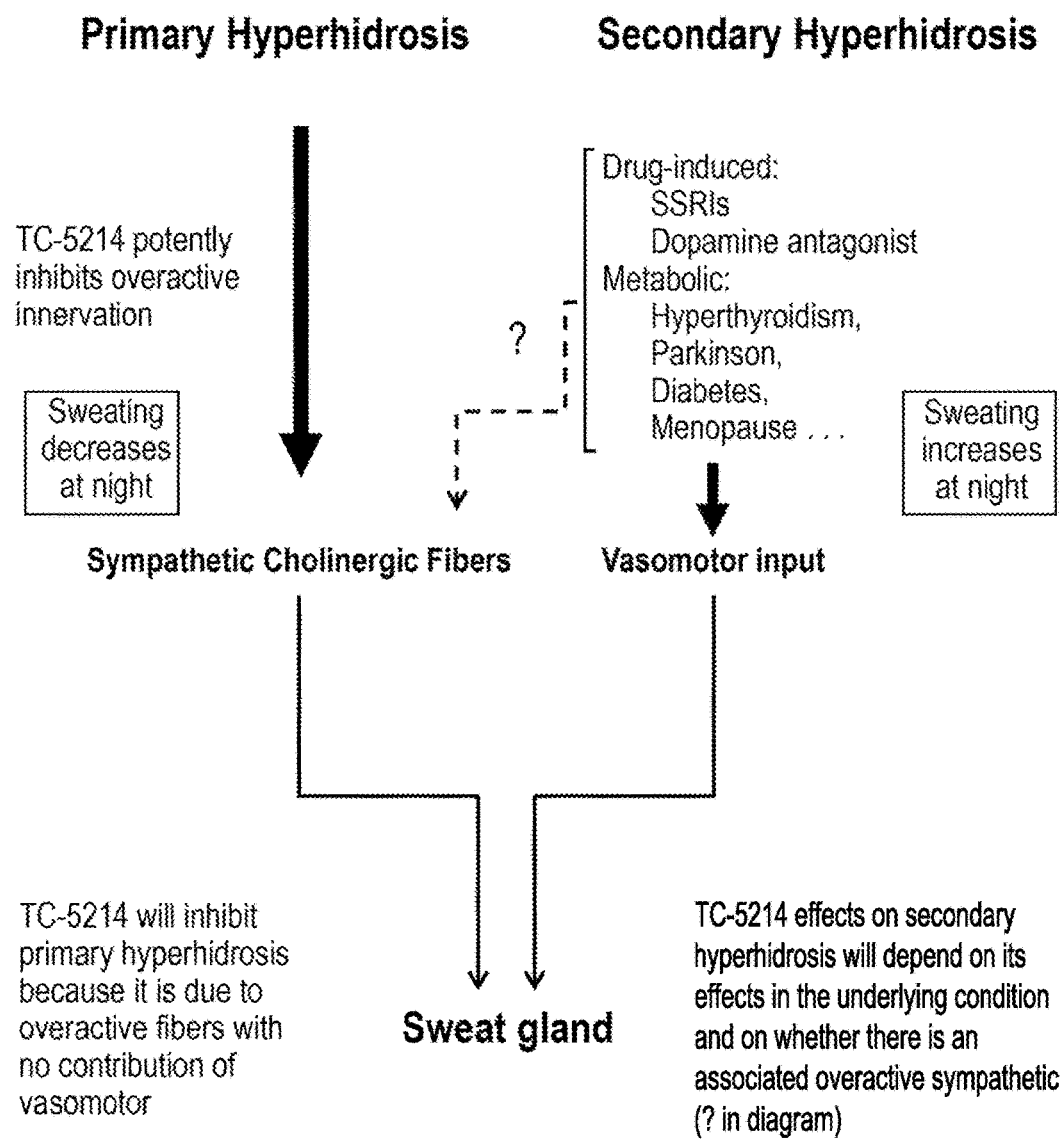
FIG. 3 illustrates a summary of hyperhidrosis etiologies.

As shown in FIG. 3, hyperhidrosis has several etiologies. For primary hyperhidrosis, TC-5214 may potently inhibit overactive innervation, thereby impacting sympathetic cholinergic fibers, with no contribution of vasomotor effects. Primary hyperhidrosis is amenable to once daily dosing of TC-5214 (0.1 to 2 mg).

Figure 4A:
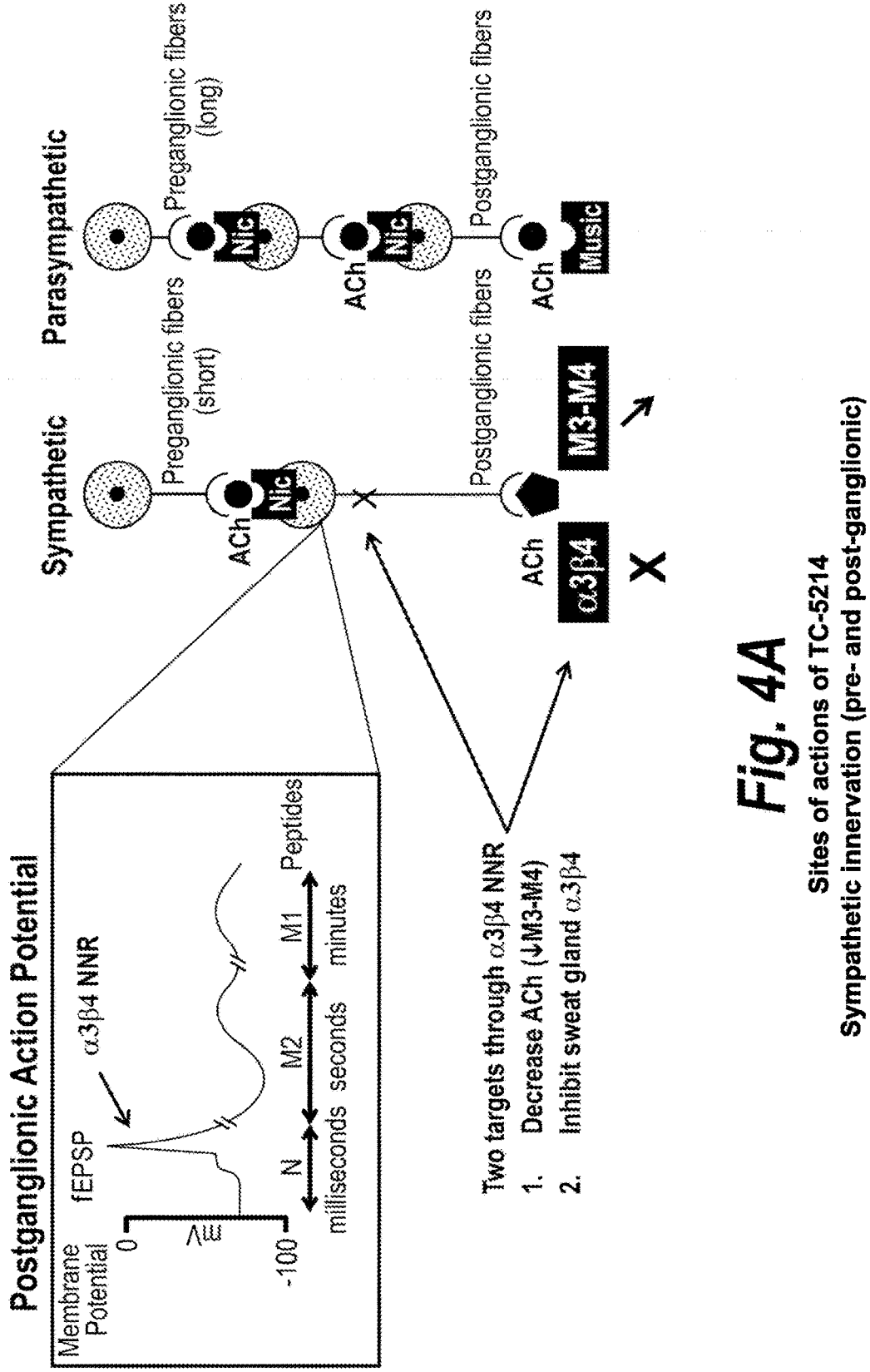
FIGS. 4A and 4B illustrate sites of actions of TC-5214.
Figure 4B:
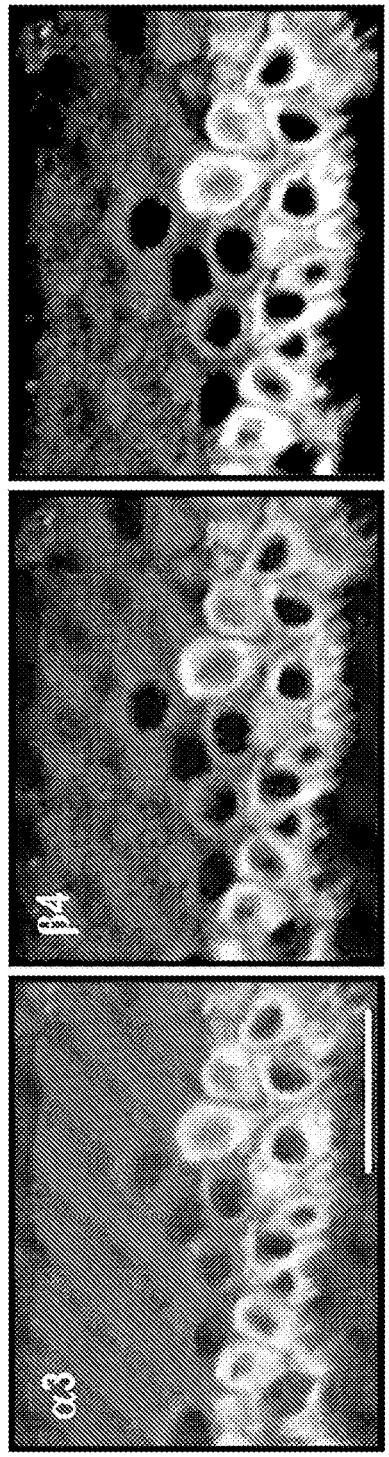

As shown in FIGS. 4A and 4B, sweat glands are expressed throughout the body, in contrast to other targets of the autonomic nervous system, sweat glands are innervated only through the sympathetic "cholinergic" fibers (i.e. releases acetylcholine from both pre- and postganglionic terminals). Nicotinic receptors ($\alpha3\beta4$) play a central role in this pathway through the fast activation of the fibers in releasing ACh, the postganglionic ACh targets on the sweat glands (nicotinic $\alpha3\beta4$ and muscarinic receptors M3 and M4).

TC-5214 will be tested to determine whether there is a therapeutic effect to potently inhibit the overactive sympathetic fibers in primary hyperhidrosis, and also decrease the acetylcholine released (a postsynaptic muscarinic component) and the ganglionic nicotinic receptors expressed on the sweat glands ($\alpha3\beta4$).

Figure 5:
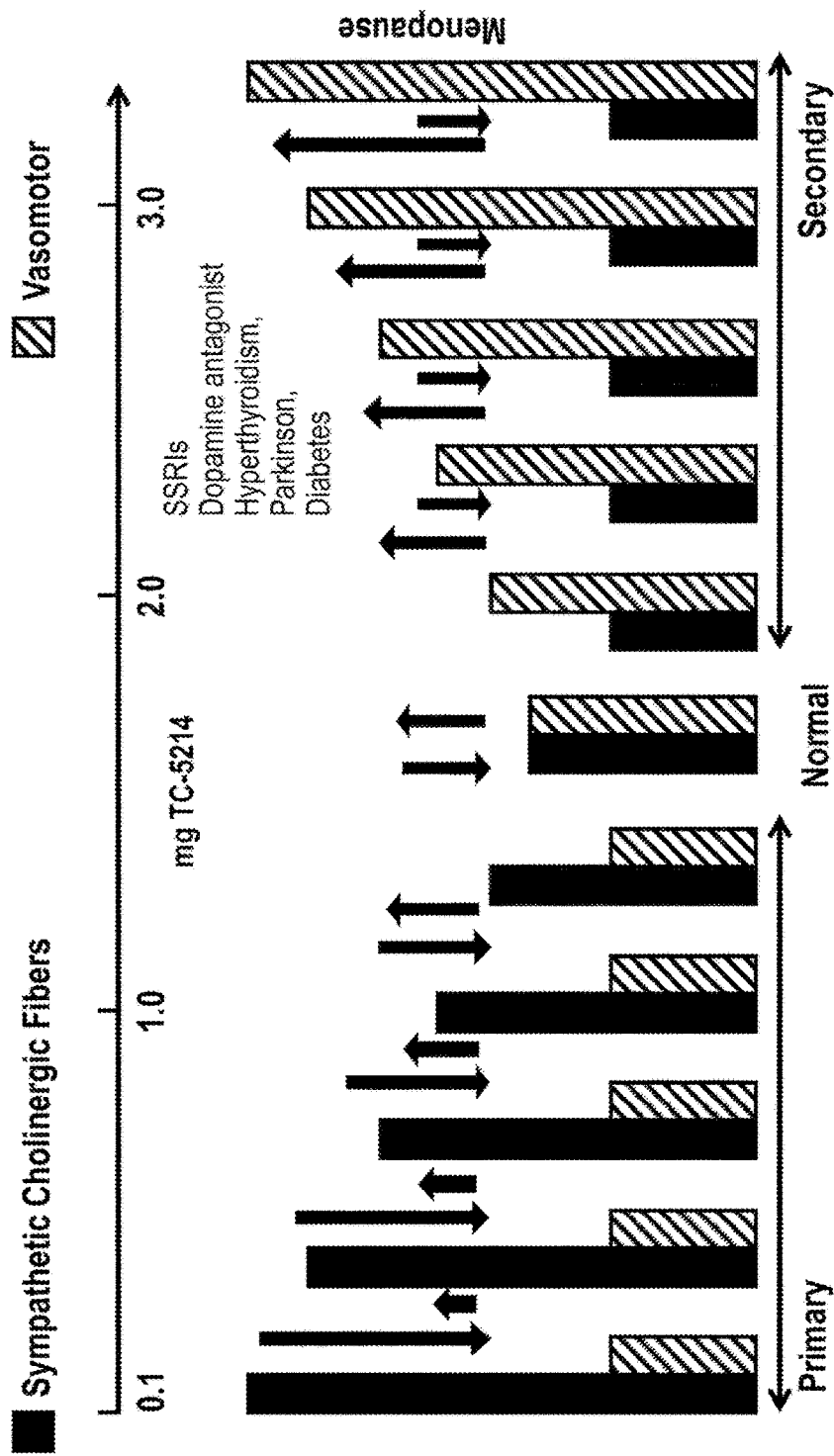
FIG. 5 illustrates a contrast between primary and secondary hyperhidrosis (sympathetic and vasomotor contribution).

Once a day dosing with TC-5214 in humans (0.1 to 2 mg) may inhibit the overactive TC-5214-sensitive sympathetic innervation to the sweet gland (blue histograms in the FIG. 5 magnitude of effects shown as black arrows) without effects on vasomotor changes (red histograms in FIG. 5; magnitude of effects shown as upward purple arrows) thereby resulting in decreased sweating.

Higher concentrations are also hypothesized to increase vasomotor changes, which already perturbed in secondary hyperhidrosis) which may have no effect or even aggravate secondary hyperhidrosis (e.g., menopause, SSRI, and other secondary causes). TC-5214 is believed to ameliorate primary hyperhidrosis at low doses (0.1 to 2 mg once a day).

Example 2: Contrasting Primary Hyperhidrosis and Overactive Bladder

As noted hereinabove, a clinical study was performed to evaluate the safety, tolerability, and efficacy of dexmecamylamine (TC-5214) for the treatment of Overactive Bladder (OAB). The study included a three- or five-week screening period, followed by a 12-week treatment period during which patients received either one of three doses of dexmecamylamine or placebo twice daily, randomized in a ratio of 2:1:1:1 (placebo, low dose, mid dose, high dose), with a two-week follow-up period. A total of 768 subjects with overactive bladder were randomized into the double-blind treatment period of the study. In the that, the high dose of TC-5214 demonstrated mixed results on the co-primary endpoints by providing a statistically significant reduction in micturition frequency (p=0.033) and an improvement that did not reach statistical significance on episodes of urinary incontinence (p=0.379) per 24 hours, alter 12 weeks of treatment. As a consequence of these results, Targacept discontinued further development of TC-5214 in OAB. In this trial, TC-5214 was considered generally safe and well tolerated. There was a placebo-corrected 15.1% rate of constipation and a 5.9% rate of urinary tract infection in the high dose group. See also, PCT Application No. PCT/US2013/030640, which published as WO 2013/142162A1.

Figure 6:
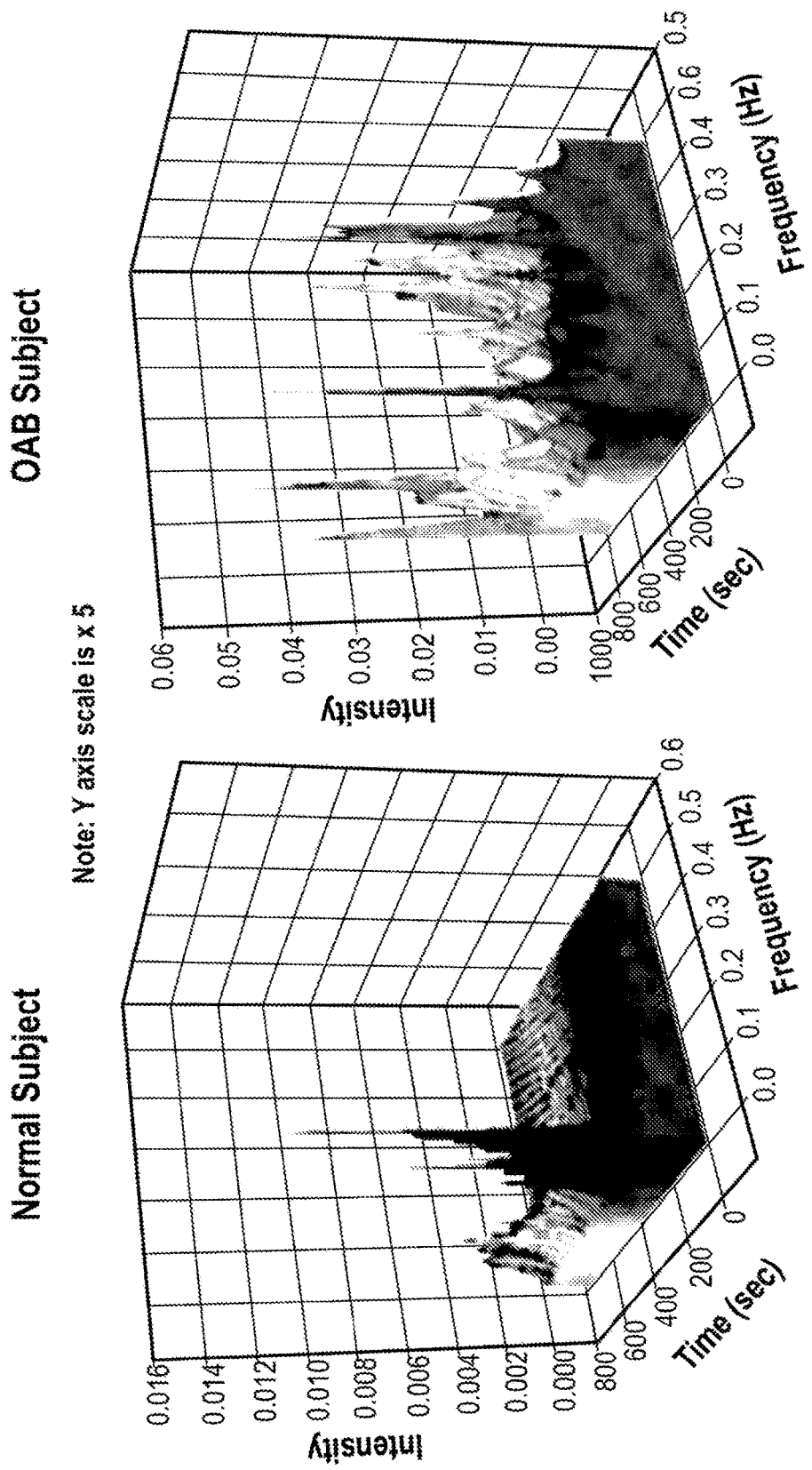
FIG. 6 illustrates overactive parasympathetic and sympathetic in a patient population of overactive bladder; thereby illustrating that the results observed so the overactive bladder study support a hypothesis for use in hyperhidrosis.

Spectral density analysis of patients with OAB shows a marker increase in the firing frequencies of both sympathetic and parasympathetic fibers in OAB; two systems that are antagonistic in bladder regulation resulting in relaxation and contraction, respectively. See FIG. 6. As illustrated, inhibition of overactive sympathetic fibers (which is not desired in OAB) will have a detrimental effect, but the inhibition of overactive parasympathetic fibers at slightly higher concentrations than those needed for sympathetic inhibition will result in inhibition of afferent signaling.

The net effect will be evident only at doses when the parasympathetic inhibition starts to compensate for the negative impact of sympathetic inhibition. Thus, in primary hyperhidrosis only the more sensitive system is operational without being counterbalanced by an antagonistic system (i.e., absence of parasympathetic signaling, which decreases sweating).

As illustrated in FIG. 7, one theoretical outcome comparing OAB and hyperhidrosis supports the failure of efficacy in OAB to support a potential for improvement in hyperhidrosis; namely that sympathetic and parasympathetic innervation occurs to the bladder and sympathetic innervation occurs only to the sweat glands. In other words, sympathetic innervation has a weak contribution to relaxation and is slightly more sensitive to TC-5214 than the parasympathetic system, which has a strong contribution to contraction of the bladder. For OAB, the effects are mediated through control of 2 antagonistic overactive pathways: the sympathetic pathway, which is more sensitive to TC-5214, but less powerful than the parasympathetic pathway. Lower doses of TC-5214 should have counteracting effects and the progressive inhibition of the overactive parasympathetic pathway tilts the balance toward relaxation but comes at a cost, namely constipation and urinary infection among the side effects. For primary hyperhidrosis, however, there is one overactive pathway, the sympathetic pathway, which is sensitive to TC-5214.

Example 3

The specific pharmacological responses observed may vary according to and depending on the particular active compound, including a particular salt form, selected or whether there are present pharmaceutical carriers, as well as the type of formulation and mode of administration employed, and such expected variations or differences in the results are contemplated in accordance with practice of the present invention.

Although specific embodiments of the present invention are herein illustrated and described in detail, the invention is not limited thereto. The above detailed descriptions are provided as exemplary of the present invention and should not be construed as constituting any limitation of the invention. Modifications will be obvious to those skilled in the art, and all modifications that do not depart from the spirit of the Invention are Intended to be Included with the scope of the appended claim.

What is claimed is:

1. A method of treating hyperhidrosis, the method comprising the administration of a therapeutically effective amount of dexmecamylamine or a pharmaceutically acceptable salt thereof, substantially free of exo-R-mecamylamine, to a subject with hyperhidrosis.

2. The method of claim 1, wherein the administration of dexmecamylamine or a pharmaceutically acceptable salt thereof substantially free of exo-R-mecamylamine, is once daily.

3. The method according to claim 1, wherein the dexmecamylamine or a pharmaceutically acceptable salt thereof is orally administered in an amount of about 4 mg.

4. The method according to claim 1, wherein the dexmecamylamine or a pharmaceutically acceptable salt thereof is orally administered in an amount of about 0.5 mg.

5. The method according to claim 1, wherein the dexmecamylamine or a pharmaceutically acceptable salt thereof is orally administered in an amount of about 1.0 mg.

6. The method according to claim 1, wherein the dexmecamylamine or a pharmaceutically acceptable salt thereof is orally administered in an amount of about 2.0 mg.

7. The method according to claim 1, wherein the dexmecamylamine or a pharmaceutically acceptable salt thereof is orally administered in tablet form.

8. The method of claim 1, wherein the administration of dexmecamylamine is sufficient to affect sweating in a patient in at least one location with an Hyperhidrosis Disease Severity Scale change of ≥1.

9. The method according to claim 8, wherein the administration of dexmecamylamine is sufficient to affect sweating in a patient in at least two locations with an HDSS change of ≥0.5, in each location.

10. The method according to claim 8, wherein the location is selected from axillary, palmoplantar, face/scalp, or generalized.

11. The method according to claim 1, wherein the hyperhidrosis is primary hyperhidrosis.

12. The method according to claim 1, wherein the subject is a human.

13. The method of claim 1, wherein the dexmecamylamine or a pharmaceutically acceptable salt thereof is administered more than once daily.

14. The method of claim 1, wherein the hyperhidrosis is palmoplantar.

15. The method of claim 6, wherein the dexmecamylamine or pharmaceutically acceptable salt thereof is administered more than once daily.

16. The method of claim 1, wherein the hyperhidrosis is secondary hyperhidrosis.

17. The method of claim 1, wherein the hyperhidrosis is secondary to spinal cord injury.

18. The method of claim 1, wherein the hyperhidrosis results from increased sympathetic cholinergic activity.

* * * * *